United States Patent
Curley et al.

(10) Patent No.: US 6,328,735 B1
(45) Date of Patent: *Dec. 11, 2001

(54) THERMAL ABLATION SYSTEM

(75) Inventors: Michael G. Curley, Cambridge; Patrick S. Hamilton, Newton, both of MA (US)

(73) Assignee: E.P., Limited, Somerville, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/183,461

(22) Filed: Oct. 30, 1998

(51) Int. Cl.[7] .............................. A61B 18/14; A61B 18/22
(52) U.S. Cl. ................. 606/41; 606/14; 606/15; 607/99; 607/105; 607/113
(58) Field of Search .................... 606/41, 14, 15; 607/99, 105, 113

(56) References Cited

U.S. PATENT DOCUMENTS

| | | | |
|---|---|---|---|
| 5,293,868 | * 3/1994 | Nardella | 606/46 |
| 5,334,193 | * 8/1994 | Nardella | 606/41 |
| 5,348,554 | 9/1994 | Imran et al. | |
| 5,398,683 | * 3/1995 | Edwards et al. | 607/116 |
| 5,431,649 | 7/1995 | Mulier et al. | |
| 5,609,151 | 3/1997 | Mulier et al. | |
| 5,769,846 | * 6/1998 | Edwards et al. | 606/41 |
| 5,876,398 | * 3/1999 | Mulier et al. | 606/41 |
| 5,891,094 | * 4/1999 | Masterson et al. | 604/113 |
| 5,902,328 | * 5/1999 | LaFontaine et al. | 607/116 |

OTHER PUBLICATIONS

Sunil Nath and David E. Haines, "Progress In Cardiovascular Diseases", vol. XXXVII, No. 4 (Jan./Feb.), 1995, pp. 185–204.

Curley, M.G. and Hamilton, P.S., "Creation of Large Thermal Lesions In Liver Using Saline–Enhanced RF Ablation", 19th International Conference—IEEE/EMBS, Oct. 30–Nov. 2, 1997, Chicago, IL, USA.

* cited by examiner

Primary Examiner—Lee Cohen
(74) Attorney, Agent, or Firm—Cesari and McKenna, LLP (57) ABSTRACT

A method and system for therapeutically treating a selected volume of tissue with a heated liquid. A therapeutic device, such as a catheter, is coupled to a source of liquid is heated to therapeutic temperatures by a heating mechanism. The device imparts thermal energy into the tissue while simultaneously injecting the heated liquid into the tissue. In a preferred embodiment, the device includes at least one electrode for conducting a radio-frequency current through the tissue in conjunction with the infusion of heated saline solution to selectively destroy the tissue.

20 Claims, 6 Drawing Sheets

THERMAL ABLATION SYSTEM

FIELD OF THE INVENTION

The present invention relates generally to the therapeutic treatment of tissue and more particularly to the use of thermal energy to create tissue lesions.

BACKGROUND OF THE INVENTION

The treatment of bodily tissue with thermal energy to destroy it is useful for various therapeutic procedures. Thermal energy can be imparted to tissue using radio frequency electrical energy, microwave or lightwave electromagnetic energy, or ultrasonic vibrational energy. Each of these is absorbed by tissue and is converted to thermal energy or heat. Tissue can also be heated through conduction, in which a heated object is placed against tissue and from which the thermal energy is conducted into the tissue. One disadvantage associated with the application of these forms of energy is that the maximum heating often occurs at the interface between the therapeutic tool and the tissue. Radio frequency (RF) heating, for example, is effected by placing one or more electrodes against tissue to be treated and passing high frequency electrical current into the tissue. The current can flow between closely spaced emitting electrodes or between an emitting electrode and a larger, common electrode located remotely from the tissue to be heated. The maximum heating often occurs in the local tissue, immediately adjacent the emitting electrodes. This often causes the local tissue to desiccate, thereby reducing its electrical conductivity. As the tissue conductivity decreases, the impedance to current passing from the electrode to the tissue increases so that more voltage must be supplied to the electrodes to affect the surrounding, more distant tissue. The tissue temperature proximate to the electrode may approach 100° C., so that water within the tissue boils to become water vapor. As this desiccation and/or vaporization process continues, the impedance of the local tissue rises so that a therapeutic level of current is not allowed to pass into the surrounding tissue.

Thus, conventional RF instruments are limited in the volume of tissue that can be treated, i.e., in the size of the thermal lesions they can create. Specifically, it is known that the level of tissue heating is proportional to the square of the electrical current density, and that the electrical current density in tissue generally falls as the square of the distance from the electrode. Therefore, the heating in tissue generally falls as the fourth power of distance from the electrode and the resulting tissue temperature therefore decreases rapidly as the distance from the electrode increases. This rapid fall-off in tissue temperature limits the volume of tissue that can be therapeutically treated using RF energy. While radio frequency (RF) electrodes can be repeatedly repositioned to treat additional tissue, the precise movement required for this task is time consuming.

The excessive heating that occurs around an RF electrode can be exacerbated by the use of metal as the emitting electrode. It is well-known that a voltage differential occurs when a metal contacts the saline solution in tissue and that current passing through a voltage differential causes energy to be dissipated at that interface. The voltage differential is a function of the specific metal and of the magnitude and direction of current flowing between the electrode and the tissue. Therefore, when the RF current passes through this voltage differential, an additional amount of energy is dissipated to produce a further increase in the temperature of the local tissue.

Attempts have been made to provide an RF device that increases lesion size. For example, existing RF instruments have been modified by increasing the electrode size or using multiple emitting electrodes. While such devices may provide some incremental increase in lesion size, larger tissue treatment volumes are desired. Other methods attempt to cool the tissue in the vicinity of the electrodes by circulating cool, i.e. body temperature (37° C.) or lower than body temperature, water against or through the electrode and on into or against the nearby tissue being heated. Imran et al. describe one such device in U.S. Pat. No. 5,348,554. The device is a catheter with a metal RF electrode disposed at the distal end of the catheter. The catheter has a channel disposed within it, extending from the proximal end of the catheter to the electrode at the distal end. When the electrode is deployed against a body tissue, an RF electrical current is passed between the distal emitting electrode and a larger, counter electrode placed at some other location on the patient's body. Sterile saline solution is simultaneously passed through the catheter channel, which passes out of the catheter and against the tissue near the electrode. The flowing saline solution cools the tissue immediately adjacent to the electrode and moderates the excessive temperature this tissue would otherwise achieve. However, it does not significantly alter the temperature of the tissue even a short distance from the electrode, so that tissue can still overheat and limit the total size of the thermal lesion that can be created.

Mulier et al. describe a similar catheter in U.S. Pat. No. 5,431,649. The catheter includes a metal RF electrode at the distal end and an internal channel extending from the proximal end to the electrode. The catheter is deployed through the vasculature and into the heart. It is then inserted directly into the tissue to be treated and an RF current is passed between the catheter electrode and a larger, counter electrode remotely located on the patient's body. Cool sterile saline solution or body-temperature sterile saline solution is passed through the channel and into the tissue through the electrode. The saline solution cools the tissue most proximate to the electrode and convects the thermal energy it absorbs from this tissue into tissue located remotely from the electrode. This can create larger thermal lesions because of the cooling combined with the improved thermal transport in the tissue. However, this method can cause excessive cooling of the tissue and can actually decrease the size of the thermal lesion created or eliminate it entirely.

It is known that there is a time-temperature relationship in the thermal destruction of tissue. A threshold temperature for causing irreversible thermal damage to tissue is generally accepted to be about 41° C. It is also known that the time required to achieve a particular level of cell necrosis decreases as the treatment temperature increases further above 41° C. It is understood that the exact time/temperature relationship varies by cell type, but that there is a general relationship across many cell types that can be used to determine a desired thermal dose level. This relationship is commonly referred to as an equivalent time at 43° C. expressed as $$t_{eq,43° C.} = \int R^{(T(t)-43°)} dt \qquad (1)$$

where T is the tissue temperature, and R is a unitless indicator of therapeutic efficiency in a range between 0 and 5 (typically 2). Note that R is zero for temperatures below 41° C. Thermal doses in the range of $t_{eq,43° C.}$=20 minutes to 1 hour are generally accepted as therapeutic. Thus, therapeutic temperature may refer to any temperature in excess of 41° C., but the exact threshold is determined by the desired therapy duration and equation (1). For example, Nath, S. and Haines, D. E., *Prog Card Dis* 37(4):185–205 (1995) (Nath et al.) suggest a temperature of 50° C. for one minute as therapeutic, which is an equivalent time at 43° C. of 128 minutes with R=2. For maximum efficiency, the therapeutic temperature should be uniform throughout the tissue being treated so that the thermal dose is uniformly delivered.

Therefore, it is desirable to provide a device for the therapeutic treatment of tissue that creates a relatively large lesion size, eliminates overheating at the interface between the therapeutic tool and the tissue, and produces an approximately equal therapeutic temperature throughout the volume of tissue being treated.

SUMMARY OF THE INVENTION

The inventive system for therapeutically treating a volume of tissue includes a source of energy, an emitter for imparting the energy into the tissue so as to raise the temperature of the tissue, a source of heated liquid, and a means for simultaneously injecting the heated liquid into the tissue at or near the emitter. The infusion of heated liquid convects the thermal energy deeper into the tissue to produce a large lesion.

In a preferred embodiment, a catheter-type therapeutic device is inserted into a patient and a distal end is placed into the target tissue. Thermal energy is imparted into the tissue by conducting radio-frequency current into the tissue through one or more emitter electrodes disposed in the distal end. Warm saline solution, which is heated to a therapeutic temperature by a mechanism that may be disposed external to or within the device, is simultaneously released into the tissue through one or more apertures disposed in the distal end. The heated saline solution reduces the charring and impedance rises normally occurring in treated tissue and convects the thermal energy deeper into the tissue. Furthermore, the overheating that typically occurs at the interface between the electrodes and the tissue is largely eliminated by forming the electrodes from a metal salt, such as silver/silver chloride. Although the invention is primarily shown and described as a catheter-type therapeutic device applying both RF current and warm saline solution to the tissue, it is understood that the invention may substitute alternative forms of energy and certain other sufficiently heated liquids, and is generally applicable to a variety of therapeutic instruments used in medical procedures where tissue is to be treated.

BRIEF DESCRIPTION OF THE DRAWINGS

The invention will be more fully understood from the following detailed description taken in conjunction with the accompanying drawings, in which.

DETAILED DESCRIPTION OF AN ILLUSTRATIVE EMBODIMENT

Figure 1:
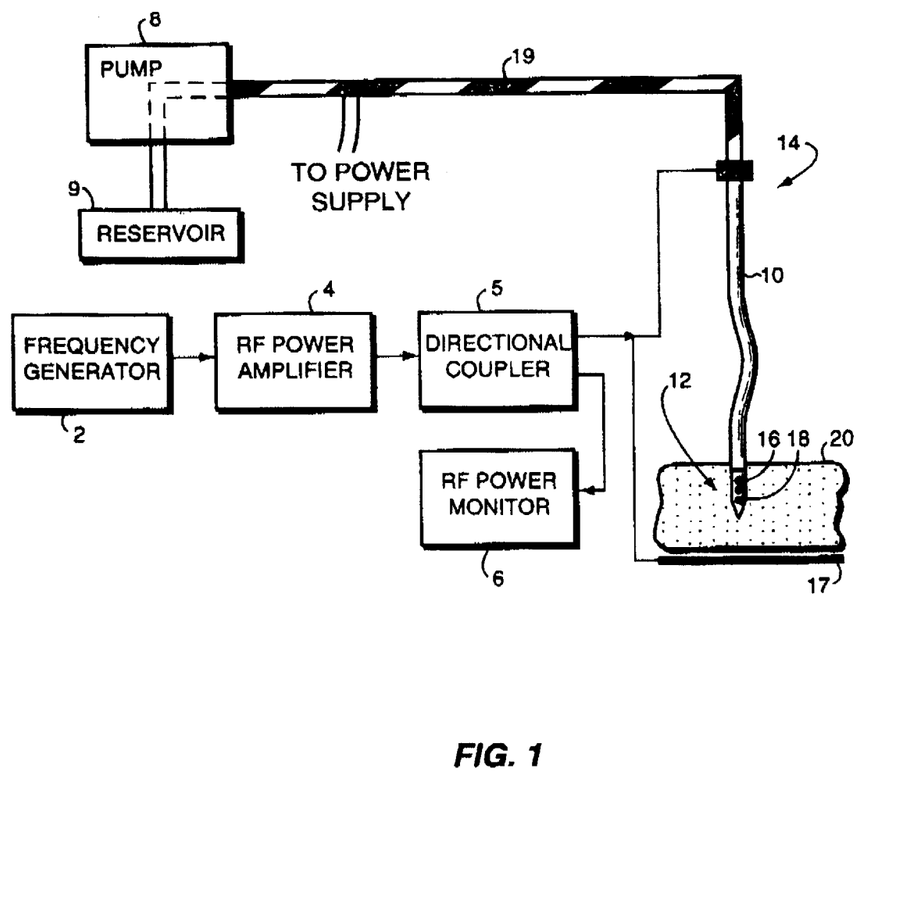
FIG. 1 is an embodiment of a system incorporating the invention.

A block diagram of a system incorporating the present invention for treating tissue is shown in FIG. 1. The system uses a catheter 10 to apply energy in the form of a radio frequency (RF) current and thereby heat the target tissue 20 to a temperature sufficient to destroy it. While the RF current is being imparted into the tissue, a warm saline solution is simultaneously injected to more evenly distribute the heat throughout the tissue.

The total length of the catheter will typically vary between 40 cm and 200 cm, depending on the location of the tissue to be heated. In an exemplary embodiment, the length of the catheter is approximately 120 cm. The catheter is generally eight French (Fr.). ("French" is a unit of measure used in the catheter industry to describe the size of a catheter and is equal to three times the diameter of the catheter in millimeters.) An emitter electrode 16 having a plurality of apertures 18 is disposed at the distal end 12 of the catheter 10. An internal liquid channel (not shown) extends from the proximal end 14 to the apertures 18 at the distal end 12. Similarly, an internal signal cable (not shown) extends from the proximal end 14 to the electrode 16.

A radio frequency (RF) signal of known amplitude and frequency is produced by a frequency generator 2. The signal is amplified by an RF power amplifier 4 into a relatively high-voltage, high-amperage signal, e.g. 50 V, 1 A. During system operation an RF current flowing between the catheter electrode 16 and a larger, counter electrode 17 located remotely on the patient's body heats the target tissue 20 around the electrode 16. It is well known that this heating is caused by the tissue's inherent electrical resistivity. The directional coupler 5 feeds a portion of the signal to a power monitor 6 to permit adjustment of the signal power to a recommended treatment level.

A pump 8 is connected to a saline solution reservoir 9. A strip heater 19 heats the saline solution as it is pumped from the reservoir 9 to the catheter 10. The reservoir 9 may be a remote supply, or preferably it may be located in proximity to, or integral with, the pump 8 and hold a predetermined amount of saline solution for a given procedure. The pump 8 may be a syringe-type pump that produces a fixed volume flow with advancement of a plunger (not shown). An example of such a pump is Model 74900 sold by Cole-Palmer Corporation of Chicago, Ill. Other types of pumps, such as a diaphragm pump, may also be employed.

The warm saline solution is pumped into the tissue through the apertures 18 while the RF current is being imparted. This convects the heat deeper into the tissue 20, thereby reducing the charring and impedance change in tissue near the electrode 16. Although the preferred liquid is readily-available, sterile normal saline solution (defined as a salt-containing solution), other liquids may be used, including Ringer's solution, or concentrated saline solution. A liquid is selected to provide the desired therapeutic and physical properties when applied to the target tissue and a sterile liquid is recommended to guard against infection of the tissue. The liquid must be capable of storing thermal energy, preferably at least as much thermal energy per unit volume as the tissue the device is intended to heat. In certain embodiments of the invention, the liquid must also be capable of conducting electricity.

The electrodes can be formed from a variety of materials that are suitable for conducting current. Any metal or metal salt may be used. Exemplary metals include stainless steel, platinum, gold or silver, and exemplary metal salts include silver/silver chloride. In a preferred embodiment, the electrodes are formed from silver/silver chloride. It is known that metal electrodes assume a voltage potential different from that of surrounding tissue and/or liquid. Passing a current through this voltage difference results in energy dissipation at the electrode/tissue interface, thereby exacerbating excessive heating of the tissue near the electrodes. In contrast, silver/silver chloride electrodes participate in a reversible exchange of electrons between the silver and chloride ions and silver-chloride molecules. The electrodes thus provide a high exchange current density so that significant currents can flow without a significant voltage drop across the electrode. Thus, an electrode formed from a metal salt such as silver/silver chloride reduces excessive energy generation at the tissue interface and thereby produces a more desirable therapeutic temperature profile even where there is no liquid flow about the electrode.

Figure 2:
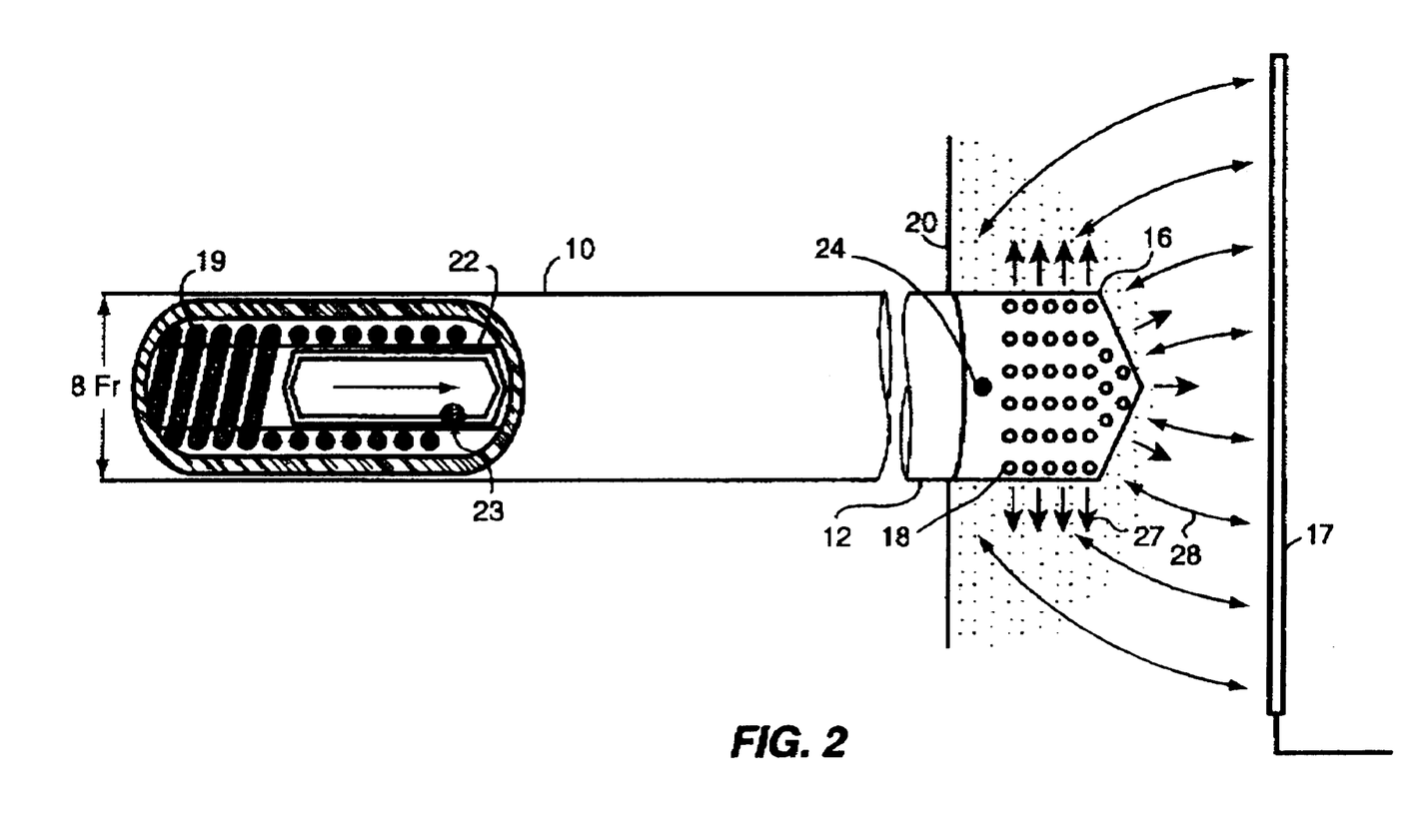
FIG. 2 is an enlarged view of an RF catheter having a resistive mechanism built into the catheter for heating liquid as it is used during therapeutic treatment of tissue.

An enlarged view of the catheter 10, as it is used to treat the target tissue 20, is shown in FIG. 2. In this embodiment of the invention, the catheter includes a resistive coil 29 surrounding the internal liquid channel 22 for heating the liquid in addition to, or as an alternative to, the strip heater 19 of FIG. 1. The dimensions of the internal liquid channel 22 can vary in accordance with the intended application, space considerations, flow rate, liquid temperature, and heating mechanism. It is understood that one of ordinary skill in the art can readily modify the channel to suit particular requirements. In an exemplary embodiment, the channel 22 has a diameter of approximately six Fr. and is surrounded by resistive coil 29 for a length of approximately 15 mm. The resistive coil 29 is comprised of nichrome wire and the coil resistance is preferably 50Ω.

The distal end 12 of the catheter 10 is shown inserted into the tissue 20 to be treated. As described above, an RF current 28 generated by the RF power amplifier (not shown) is passed from the catheter electrode 16 through the target tissue 20 to the remote electrode 17. As saline solution is pumped through the catheter, it is heated above body temperature, preferably to 50° C., by the resistive coil 19 heater. This is accomplished by connecting the resistive coil 29 to a DC power supply (not shown) via wires (not shown) that are disposed within the catheter 10 and exit at the proximal end (not shown). Applying 21.5 V to the resistive coil 29 will be sufficient to heat liquid flowing at 10 ml/min to 50° C. The heated, flowing saline solution 27 is injected into the tissue simultaneously with the RF current via the apertures 18 at a rate of 10 ml/min.

The heated, flowing saline solution 27 exits in a direction that is preferably perpendicular to the heating field such that the area of tissue heated by the applied RF current 28 is perfused with the current-conducting saline solution. The concurrent application of RF energy and perfusion of heated saline solution into the tissue eliminates the desiccation and/or vaporization of tissue adjacent to the electrodes, maintains the effective tissue impedance, and it increases the thermal transport within the tissue being heated with RF energy. The total volume of tissue heated to therapeutic temperatures, i.e., greater than 41°C., is thereby increased.

A first temperature sensor 23 can be located in the channel 22 for measuring the temperature of the flowing liquid 27. This sensor may also be located in the channel 22 or at any other point permitting an accurate reading of liquid temperature. A second temperature sensor 24 can be located on the distal end 12 proximate to the electrode 16 for measuring and controlling the electrode temperature. Control of electrode temperature by adjusting the applied voltage and current is well known to one of ordinary skill in the art. The temperature sensors may be selected from a variety of sensor types including thermocouples, thermistors and diodes.

Figure 3:
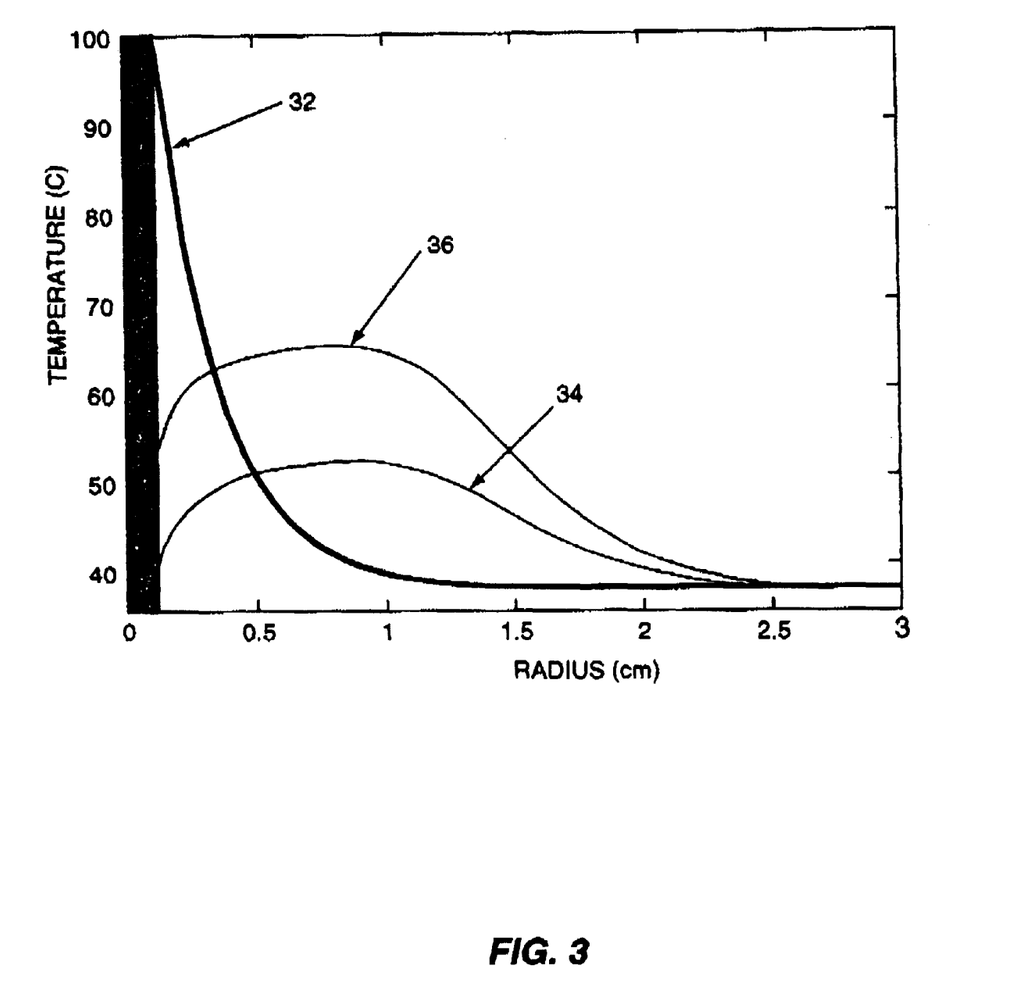
FIG. 3 is a graph of tissue temperature profiles.

Computer simulated tissue temperature profiles for three radio frequency energy systems are shown in FIG. 3. The profiles provide the tissue temperature as a function of radial distance from an RF electrode after 60 seconds of treatment. A first tissue temperature profile 32 is associated with a prior system similar to that described by Nath et al. In this system the electrode is inserted into the tissue and imparts an RF current flow of about 180 mA to heat the tissue. No liquid is applied against or into the tissue during the imparting of the RF current. The tissue temperature profile 32 falls very sharply with distance from the electrode, i.e., it falls below 50° C. only 5 mm from the electrode. As noted above, Nath et al. suggest that temperatures below 50°C. are subtherapeutic for treatment durations of one minute or less.

A second tissue temperature profile 34 is associated with a second prior system similar to that described by Mulier et al. in U.S. Pat. No. 5,431,649. In this second system the electrode is inserted into the tissue and imparts a 400 kHz RF current flow of about 525 mA to heat the tissue. Body temperature (37° C.) saline solution is simultaneously injected into the tissue at a rate of 10 ml/min. The tissue temperature profile 34 is more uniform, but the maximum temperature achieved is approximately 50° C. Thus, the temperature profile 34 exceeds the generally accepted tissue-damaging temperature threshold specified for one minute of therapy in only a small portion of the tissue. As described above, such a small temperature increment requires significant treatment time to achieve any therapeutically meaningful results.

A third tissue temperature profile 36 is achieved using the preferred embodiment of the present invention. In the inventive system an electrode formed from silver/silver chloride is inserted into the tissue and imparts a 400 kHz RF current flow of 525 mA to heat the tissue. Saline solution heated to 50° C. is simultaneously injected into the tissue at a rate of 10 ml/min. The resulting temperature profile 36 is uniform and stays significantly above the 50°C. therapeutic threshold out to 15 mm from the electrode. Because the temperature is uniform within this volume, the thermal dose delivered is also uniform through this volume.

It is understood that one of ordinary skill in the art can readily modify the exemplary embodiment described above to provide different operating parameters, such as liquid temperature, liquid flow rate, and electrode configuration. For example, although the emitter electrode 16 in the embodiment of FIG. 2 is configured as a continuous cylindrical band adapted for a monopolar current flow, the electrode can also be formed in other geometries, such as spherical or helical, that form a continuous surface area, or the electrode may have a plurality of discrete portions. The electrodes may also be configured for bipolar operation.

Figure 4:
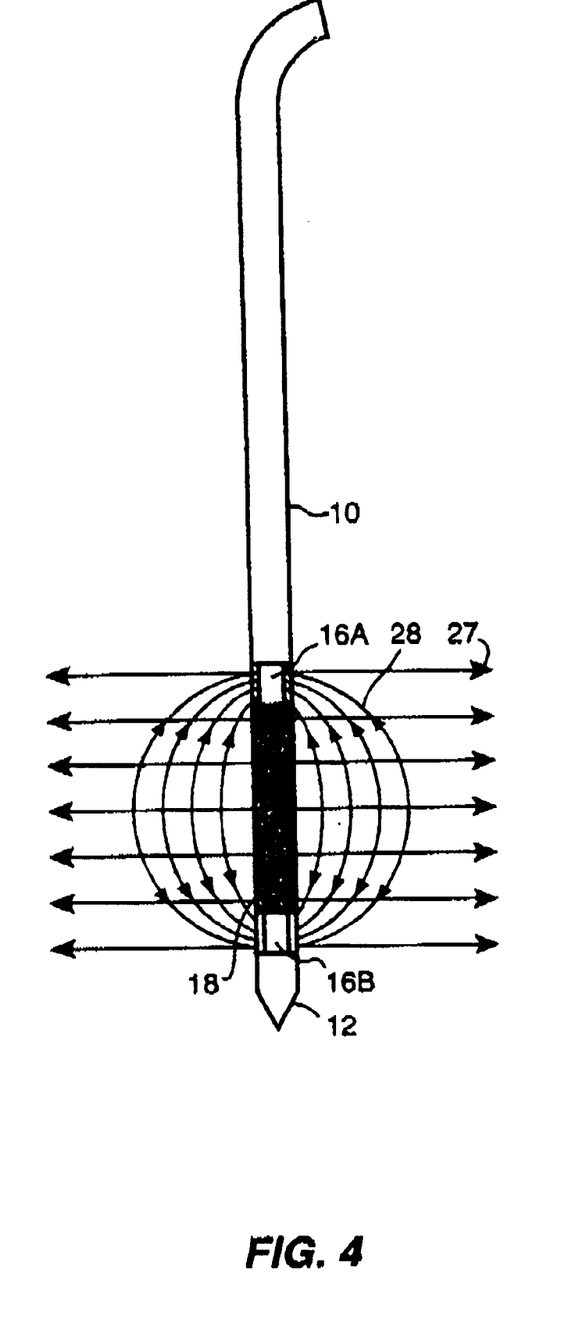
FIG. 4 is a catheter with bipolar RF electrodes incorporating the invention.

A catheter 10 adapted for bipolar RF current heating is shown in FIG. 4. A first emitter electrode 1 6A is positioned at the distal end 12 of the catheter 10, and a second emitter electrode 1 6B is positioned a certain distance away from the first electrode 16A further up the catheter 10. An RF current 28 flows axially between the two electrodes.

It is understood that an array of apertures 18 may be located in the electrodes 16A, 16B and also between the electrodes and/or extend proximally from the first electrode 16A and distally from the second electrode 16B. This array of apertures may extend for the entire distance between the electrodes or only a portion thereof. It is further understood that the apertures can direct the saline solution in a direction normal to the catheter 10 or at a proximal or distal angle. In a preferred embodiment, the aperture array extends from the proximal edge of the first electrode 16A to the distal edge of the second electrode 16B and perfuse the liquid 27 radially and substantially normal to the catheter 10.

Those that are knowledgeable in the art will recognize that the heating mechanism for producing hyperthermia within the target tissue sufficient to destroy it can include other forms of energy. Ultrasonic vibrational energy is known to be absorbed by tissue and converted to heat, as is microwave and lightwave electromagnetic energy, and alternative embodiments of the catheter may employ ultrasonic transducers, microwave antennas or lightwave diffusers as emitters disposed in the distal end of the catheter. Lightwave electromagnetic energy can fall in a range spanning visible, near-infrared, infrared, and far infrared radiation, and can be generated by filaments, arc lamps, lasers of various forms, such as diodes, semiconductors or pumps, or by other means. Similarly, the distal end can be adapted to include a heating mechanism such as a resistive wire for heating the tissue through conduction. The injection of warm liquid into the tissue proximate any of these heating devices will improve the ability of each device to heat large volumes of tissue. It is also recognized that the delivery device can be any standard medical delivery device, depending on the tissue to be treated. Alternative embodiments include metallic or nonmetallic needles, sheaths or introducers.

Figure 5:
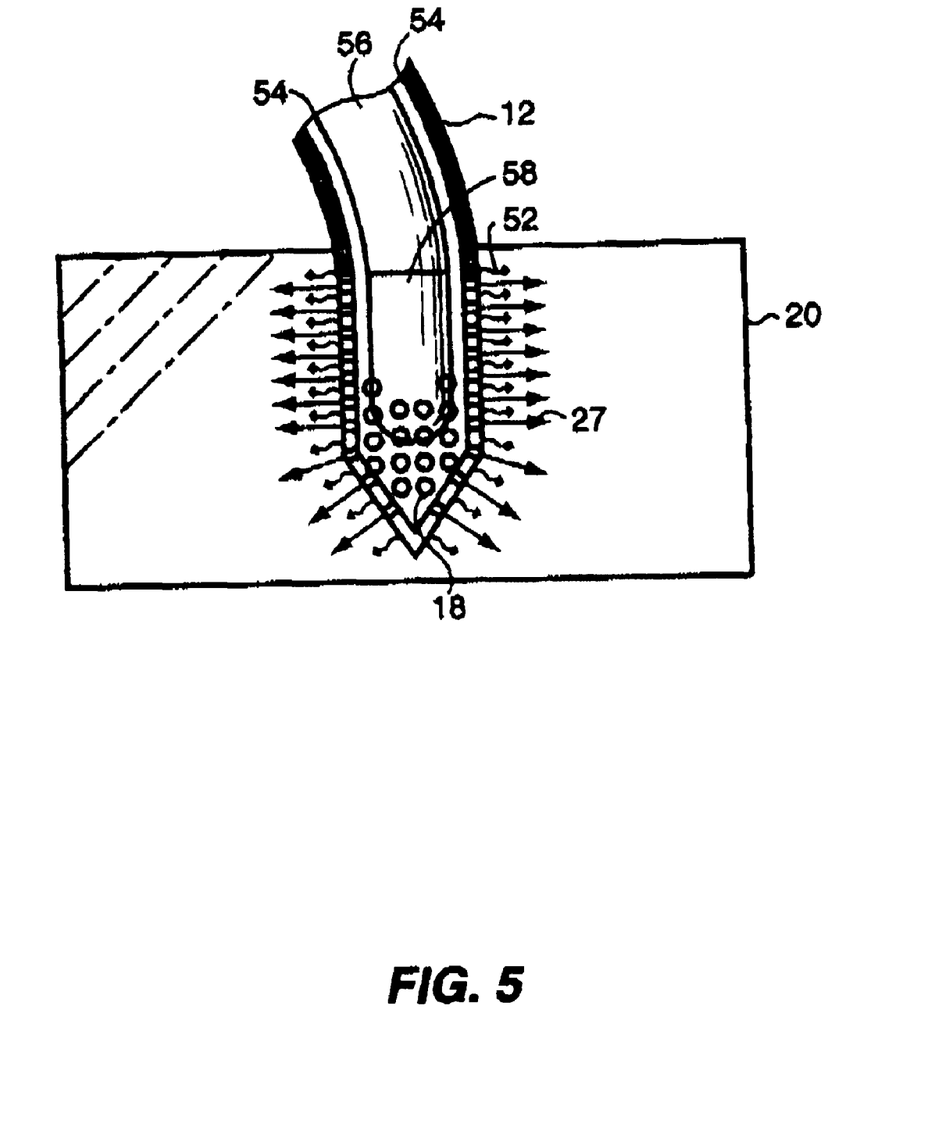
FIG. 5 is a catheter with an infrared diffuser incorporating the invention.

An alternative embodiment of this invention using lightwave radiation to treat the target tissue 20 is shown in FIG. 5. The distal end 12 of the catheter 10 is made from quartz or a similar material that is preferentially transparent to light 52 from a 940 nm laser. The distal end 12 is tapered to facilitate insertion into tissue 20 and includes a plurality of apertures 18. The catheter 10 has at least one channel 54 disposed within it and connected to a source of liquid (not shown). The liquid is heated above body temperature using one of the mechanisms described herein. The flowing liquid 27 is injected into the target tissue 20 through the plurality of apertures 18.

A fiber-optic cable 56 is disposed within the channel 54 so as to deliver lightwave energy from an external source (not shown) to an electromagnetic diffuser 58 positioned proximate to the target tissue 20. The energy source can be a diode laser emitting laser radiation, preferably in the visible to infrared ranges. One such diode laser is the H01-D060-940-FCMS laser manufactured by Opto Power Corporation in Tucson, Ariz. The fiber-optic cable and the laser diffuser in this alternative embodiment may be the Lightstic fiber and laser diffuser manufactured by Rare Earth Medical of West Yarmouth, Mass. This system is capable of delivering up to 60W of near-infrared lightwave radiation 52, which passes through the transparent catheter tip to be absorbed by tissue 20 and converted into heat and thereby raise the temperature of the tissue. Simultaneous with the laser heating, the warm, flowing liquid 27 is injected into tissue 20 to increase the thermal transport within tissue, to prevent desiccation of the tissue and thus ensure that the volume of tissue heated to therapeutic temperature is greater than that heated by the laser irradiation alone. The liquid can be heated using one of the methods described herein.

Figure 6:
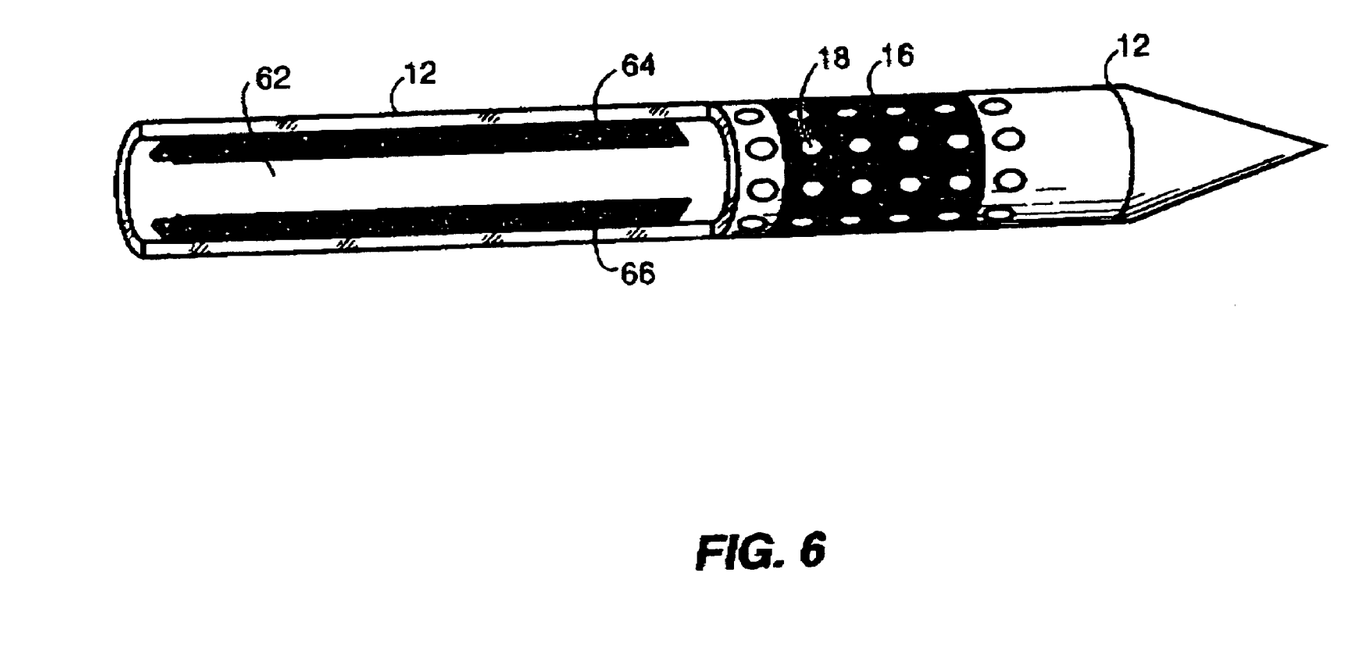
FIG. 6 is a catheter with an RF electrode having a liquid heating mechanism comprising two RF electrodes.

It is also understood that the liquid flowing through the catheter can be heated by a variety of methods in addition to the resistive mechanisms described above, depending on the liquid to be used. An embodiment of the invention having a radio-frequency liquid heating mechanism within the 8 Fr catheter 10 is shown in FIG. 6. The distal portion 12 of the catheter 10 is adapted with a conical taper for insertion into the tissue to be treated. The catheter 10 has a 6 Fr channel 22 in fluid communication with the source of liquid and the distal end 12 of the catheter 10. Disposed within the channel 22 is a heating mechanism for heating the liquid.

The heating mechanism includes a first electrode 64 and a second electrode 66 for passing a current through the liquid and thereby raising the liquid temperature. In one embodiment, the electrodes 64, 66 are formed from silver/silver-chloride and are about 2.0 millimeters wide and about 12 millimeters in length. However, it will be appreciated that the electrodes 64, 66 can be formed using a variety of materials (e.g., platinum) and configurations to heat a suitable liquid to selected temperatures at desired flow rates. The electrodes 64, 66 are coupled to an energy source via wires (not shown) disposed within the catheter 10. The energy source comprises a RF generator and amplifier and provides RF current to the two electrodes 64, 66 to heat the liquid through ohmic heating. In this embodiment, the power delivered by the electrodes can range from 25 to 125 Watts with the applied voltage between 35 and 80 volts. The electrodes 64, 66 can raise the temperature of the liquid to a temperature ranging from approximately 50° C. to 70°C. at a flow rate between about 30 and 50 ml/min. The heated liquid is provided to the distal electrode 16 for transmission into the tissue to be heated.

The liquid may also be heated using electromagnetic radiation, such as infrared or far infrared light, preferably with a wavelength greater than 1200 nm which is known to be strongly absorbed by water. The heating mechanism is a light diffuser disposed within the channel of the catheter. The light diffuser is connected to an energy source external to the catheter using a fiber-optic cable. The energy source can be a continuous wave semiconductor laser emitting electromagnetic radiation, preferably in the infrared range. One such diode laser is the OL508A-50 laser manufactured by Mas-Tech International Inc. in Randolf, N.J. The fiber-optic cable and the laser diffuser in this alternative embodiment is the Lightstic fiber manufactured by Rare Earth Medical of West Yarmouth, Mass. This system is capable of delivering up to 50W of 1550 nm radiation, which is capable of heating water-containing liquids prior to injection into tissue.

It will be obvious to those familiar with the art that other alternative embodiments for effecting the heating of the liquid include microwave radiation or high-frequency ultrasound (for liquids with strong ultrasound absorption). Alternatively, the liquid can be injected into the catheter after having been warmed prior to insertion into the external pump or while stored in the pump. In this last alternative embodiment, there is no need for a heating mechanism in the catheter itself.

One skilled in the art will realize further features and advantages of the invention from the above-described embodiments. Accordingly, the invention is not to be limited to what has been particularly shown and described, except as indicated by the appended claims. All publications and cited references are expressly incorporated herein by reference in their entirety.

What is claimed is:

1. A system for the therapeutic treatment of a volume of tissue, said system comprising an energy source;

an emitter for contacting the tissue and thereby imparting energy from the source to the tissue to raise the temperature of the tissue;

a source of liquid which can be raised to a therapeutic temperature;

a chamber forming a passage fluidly coupled to the source of liquid and the emitter, the passage having a proximal end and a distal end proximate the emitter;

means for moving the liquid from the proximal end to the distal end;

means for heating the liquid within the passage from a first temperature below the therapeutic temperature to a second temperature at least as high as the therapeutic temperature such that the liquid does not reach the therapeutic temperature prior to being proximate the distal end; and means for injecting the heated liquid into the tissue proximate to the emitter whereby the temperature of the volume of tissue is raised to a therapeutic level.

2. The system of claim 1 wherein the energy source is a radio frequency generator; and the emitter is an electrode connected to the source.

3. The system of claim 2 including a second emitter for contacting the tissue, said second emitter being a second electrode connected to the source whereby a current from the generator flows through the tissue between the electrodes.

4. The system of claim 3 wherein the emitters are metal salt electrodes.

5. The system of claim 3 wherein the emitters are silver/silver chloride electrodes.

6. The system of claim 1 wherein the energy source is lightwave generator and the emitter emits lightwave electromagnetic energy.

7. The system of claim 1 wherein the means for heating the liquid includes an electrically resistive element to conduct heat into the liquid.

8. The system of claim 1 wherein the means for heating the liquid includes means for conducting a radio frequency current through the liquid.

9. The system of claim 8, wherein the chamber has an axis and the heating means includes a pair of spaced apart electrodes disposed in the chamber at substantially the same axial position.

10. A system for the therapeutic treatment of a volume of tissue, said system comprising an energy source;

a source of liquid which can be raised to a therapeutic temperature;

an elongated catheter having distal and proximal ends, the catheter including an emitter coupled to the energy source and disposed at the distal end for contacting the tissue and thereby imparting energy from the source to the tissue to raise the temperature of the tissue, a body forming a channel fluidly coupled to the source of liquid and the emitter, the channel having a proximal end and a distal end proximate the emitter, means for transporting heated liquid in a substantially continuous flow through the channel from the proximal to the distal end and into the tissue proximate to the emitter whereby the temperature of the volume of tissue is raised to a therapeutic level, and means for heating the liquid within the channel from a first temperature below the therapeutic temperature to a second temperature at least as high as the therapeutic temperature such that the liquid does not reach the therapeutic temperature prior to being proximate the distal end.

11. The system of claim 10, wherein the heating means are disposed proximate the distal end.

12. A system for the therapeutic treatment of a volume of tissue, said system comprising an energy source;

an emitter for contacting the tissue and thereby imparting energy from the source to the tissue to raise the temperature of the tissue;

a source of liquid which can be raised to a therapeutic temperature;

a chamber forming a passage fluidly coupled to the source of liquid and the emitter, the passage having a proximal end and a distal end proximate the emitter;

means for transporting the liquid from the proximal end to the distal end;

means for heating the liquid substantially only at the distal end of the passage from a first temperature below the therapeutic temperature to a second temperature at least as high as the therapeutic temperature; and means for injecting the heated liquid into the tissue proximate to the emitter whereby the temperature of the volume of tissue is raised to a therapeutic level.

13. A method for the therapeutic treatment of a volume of tissue, comprising the steps of imparting energy from an emitter to the tissue to raise the temperature of the tissue;

providing a source of liquid which can be raised to a therapeutic temperature;

providing a chamber forming a passage fluidly coupled to the source of liquid and the emitter, the passage having a proximal end and a distal end proximate the emitter;

transporting the liquid from the proximal end to the distal end;

heating the liquid substantially only at the distal end of the passage from a first temperature below the therapeutic temperature to a second temperature at least as high as the therapeutic temperature; and injecting the heated liquid into the tissue proximate to the emitter whereby the temperature of the volume of tissue is raised to a therapeutic level.

14. The method of claim 13 wherein the energy is imparted by conducting a radio frequency current through the tissue.

15. The method of claim 10 wherein the radio frequency current is conducted into the tissue through electrodes.

16. The method of claim 11 wherein the electrodes are formed from a metal salt.

17. The method of claim 11 wherein the electrodes are formed from silver/silver chloride.

18. The method of claim 13 wherein the energy is imparted by radiating lightwave energy into the tissue.

19. The method of claim 13 wherein the liquid is heated by conducting heat produced by a resistive element into the liquid.

20. The method of claim 13 wherein the liquid is heated by conducting a radio frequency current through the liquid.

* * * * *

UNITED STATES PATENT AND TRADEMARK OFFICE
CERTIFICATE OF CORRECTION

| | | |
|---|---|---|
| PATENT NO. | : 6,328,735 B1 | Page 1 of 1 |
| APPLICATION NO. | : 09/183461 | |
| DATED | : December 11, 2001 | |
| INVENTOR(S) | : Michael G. Curley and Patrick S. Hamilton | |

It is certified that error appears in the above-identified patent and that said Letters Patent is hereby corrected as shown below:

In the Specification:

At column 1, before "BACKGROUND OF THE INVENTION," insert the following:

--GOVERNMENT RIGHTS

This invention was made with government support under grants CA69926 and HL63535 awarded by the National Institutes of Health. The government has certain rights in the invention.--

Signed and Sealed this

Eighteenth Day of September, 2012

David J. Kappos
*Director of the United States Patent and Trademark Office*